(12) United States Patent
Guo et al.

(10) Patent No.: US 10,375,997 B2
(45) Date of Patent: Aug. 13, 2019

(54) ATOMIZER AND ELECTRONIC CIGARETTE HAVING SAME

(71) Applicant: Shenzhen First Union Technology Co., Ltd., Shenzhen, Guangdong Province (CN)

(72) Inventors: Yonglu Guo, Shenzhen (CN); Zhongli Xu, Shenzhen (CN); Yonghai Li, Shenzhen (CN)

(73) Assignee: Shenzhen First Union Technology Co., Ltd. (CN)

( * ) Notice: Subject to any disclaimer, the term of this patent is extended or adjusted under 35 U.S.C. 154(b) by 135 days.

(21) Appl. No.: 15/821,757

(22) Filed: Nov. 22, 2017

(65) Prior Publication Data

US 2018/0140019 A1    May 24, 2018

(30) Foreign Application Priority Data

Nov. 24, 2016    (CN) .................... 2016 2 1266920 U

(51) Int. Cl.
*A24F 47/00*    (2006.01)
*A61M 11/04*    (2006.01)

(52) U.S. Cl.
CPC ......... *A24F 47/008* (2013.01); *A61M 11/042* (2014.02)

(58) Field of Classification Search
CPC .................................................... A24F 47/008
See application file for complete search history.

(56) References Cited

U.S. PATENT DOCUMENTS

| 2014/0109921 A1* | 4/2014 | Chen ..................... A24F 47/008 131/273 |
| 2014/0299125 A1* | 10/2014 | Buchberger ......... A61M 11/041 128/202.21 |
| 2017/0105454 A1* | 4/2017 | Li ......................... H05B 1/0244 |
| 2018/0140019 A1* | 5/2018 | Guo ...................... A61M 11/042 |
| 2018/0280636 A1* | 10/2018 | Jiang ..................... A24F 47/00 |

* cited by examiner

*Primary Examiner* — James Harvey
(74) *Attorney, Agent, or Firm* — PROI Intellectual Property US

(57) ABSTRACT

An atomizer includes a housing and a liquid storage cup. The housing has a mouthpiece thereon. The liquid storage cup is provided in the housing and configured for storing tobacco liquid. The liquid storage cup has an opening at one end thereof. A microporous liquid conducting body is plugged inside the opening for conducting the tobacco liquid in the liquid storage cup into an atomizing unit. An atomizing unit is connected to the opening and configured for heating the tobacco liquid to generate aerosol. An air flow channel is provided between the mouthpiece and the atomizing unit. The atomizing unit includes a support, a liquid guiding component located in the support, and at least one vertically arranged heating sheet. The heating sheet includes a side surface in contact with the liquid guiding component.

12 Claims, 5 Drawing Sheets

ATOMIZER AND ELECTRONIC CIGARETTE HAVING SAME

CROSS REFERENCE TO RELATED APPLICATIONS

The present application claims priority to Chinese utility model application CN 2016 212 669 20.9 filed on Nov. 24, 2016.

TECHNICAL FIELD

The utility model relates to the field of electronic cigarettes, in particular to an atomizer and a split-type electronic cigarette including the atomizer.

BACKGROUND

As an alternative to traditional cigarettes, electronic cigarettes have the advantage of environmental protection and health and are gradually accepted by consumers at home and abroad. As a main component of electronic cigarettes, the atomizer has the function of storing a certain amount of tobacco liquid and atomizing the tobacco liquid to form an aerosol for suctioning. At present, a typical atomizer in the prior art is to install an atomizing head in the liquid storage chamber, and the atomizing head is complicated in structure and costly. Under the trend of electronic cigarettes becoming more and more simple and portable, it is necessary to design an atomizer which is simple in structure and convenient to carrying and has a disposable liquid storage cup which is easy to replace. At the same time, the heating element in the existing atomizing head adopts a spiral heating wire, which has a low heating efficiency, a poor atomizing effect and an unstable aerosol volume.

SUMMARY

The technical problem to be solved by the utility model is to overcome the shortcomings of the prior art and to provide an atomizer and a split-type electronic cigarette with a simple structure and a high heating efficiency.

In order to solve the above technical problem, the utility model provides an atomizer, including: a housing having a mouthpiece thereon; a liquid storage cup provided in the housing and configured for storing tobacco liquid, the liquid storage cup having an opening at one end thereof; a microporous liquid conducting body plugged inside the opening and configured for conveying the tobacco liquid in the liquid storage cup to the atomizing unit; an atomizing unit connected to the opening and configured for heating the tobacco liquid to generate aerosol; and an air flow channel provided between the mouthpiece and the atomizing unit; wherein the atomizing unit includes a support, a liquid guiding component located in the support, and at least one vertically arranged heating sheet; the heating sheet includes a side surface in contact with the liquid guiding component, the liquid guiding component is configured to be in contact with the microporous liquid conducting body to guide the tobacco liquid to the heating sheet, and the support further defines an aerosol outlet configured for discharging the aerosol into the air flow channel.

Further, the liquid guiding component includes a first liquid guiding piece placed horizontally and a second liquid guiding piece placed vertically, the second liquid guiding piece includes a side surface attached to the heating sheet, and the first liquid guiding piece is located between the second liquid guiding piece and the microporous liquid conducting body and is horizontally attached to a bottom surface of the microporous liquid conducting body.

Quite usefully, the microporous liquid conducting body is made of PE foam material and/or PET fiber, and both the first liquid guiding piece and the second liquid guiding piece are made of non-woven fabrics material.

As one of the specific embodiments, the atomizer includes two heating sheets vertically arranged inside the support, the two heating sheets are spaced apart from each other, and each of the heating sheets matches with a correspondent one of the second liquid guiding pieces.

Further, the aerosol outlet is defined at a bottom of the support, and the aerosol outlet is aligned with the two heating sheets.

Further, a heating chamber is provided in the support, two card slots are formed on the inner wall of the heating chamber into which the heating sheets are inserted, and two of the second liquid guiding pieces are provided in the heating chamber, respectively, and are in contact with the corresponding heating sheets.

Further, the support is further provided with two electrode sheets, respectively, which are in contact with the pins of the heating sheets, and the electrode sheets include a contact part configured to be in contact with an electrode terminal of the power supply and a bending part configured for inserting into the support to fix the electrode sheets.

Further, a base is mounted in the housing, wherein the base is configured for fixing the atomizing device, the base defines two jacks aligned with the electrode sheets, and the jacks are adapted to be inserted by electrode terminals of a power supply to come into contact with the electrode sheets.

Quite usefully, the air flow channel has a size which gradually decreases from downstream to upstream, and has an air flow outlet defined between the housing and the liquid storage cup at an upstream position thereof, and the air flow outlet is communicated with the air flow channel and the mouthpiece.

Quite usefully, the heating sheet is a grid-shaped heating sheet or a mesh-shaped heating sheet.

The utility model also provides a split-type electronic cigarette including: atomizer described above; and a power supply assembly detachably connected with the atomizer, wherein the power supply assembly includes a pair of electrode terminals, and the two electrode terminals are configured for electrically connecting to the heating sheet when the power supply assembly is connected to the atomizer.

As a preferred solution, the atomizer and the power supply assembly are connected in a snap fit manner, the housing includes an annular rib in an inner edge of a lower end of the housing of the atomizer, and the annular rib is configured for forming a snap fit connection.

The beneficial effects of the utility model are mainly as follows: the liquid storage cup provided in the atomizer of the present invention is disposed inside the housing and may be integrally formed with the housing. The microporous liquid conducting body and the atomizing unit are disposed at the opening of the liquid storage cup, which is simple in structure and low in manufacturing cost. In addition, the atomizing unit adopts the design of the heating element, the heating element is vertically arranged and has a side surface in contact with the liquid guiding component, which may increase the contact area with the liquid guiding component, improve the heating efficiency, and have a good atomizing effect and a good aerosol volume stability.

DETAILED DESCRIPTION

The specific structure of the atomizer and the split-type electronic cigarette and the principle of using the same will be further elaborated below with specific embodiments.

Figure 1:
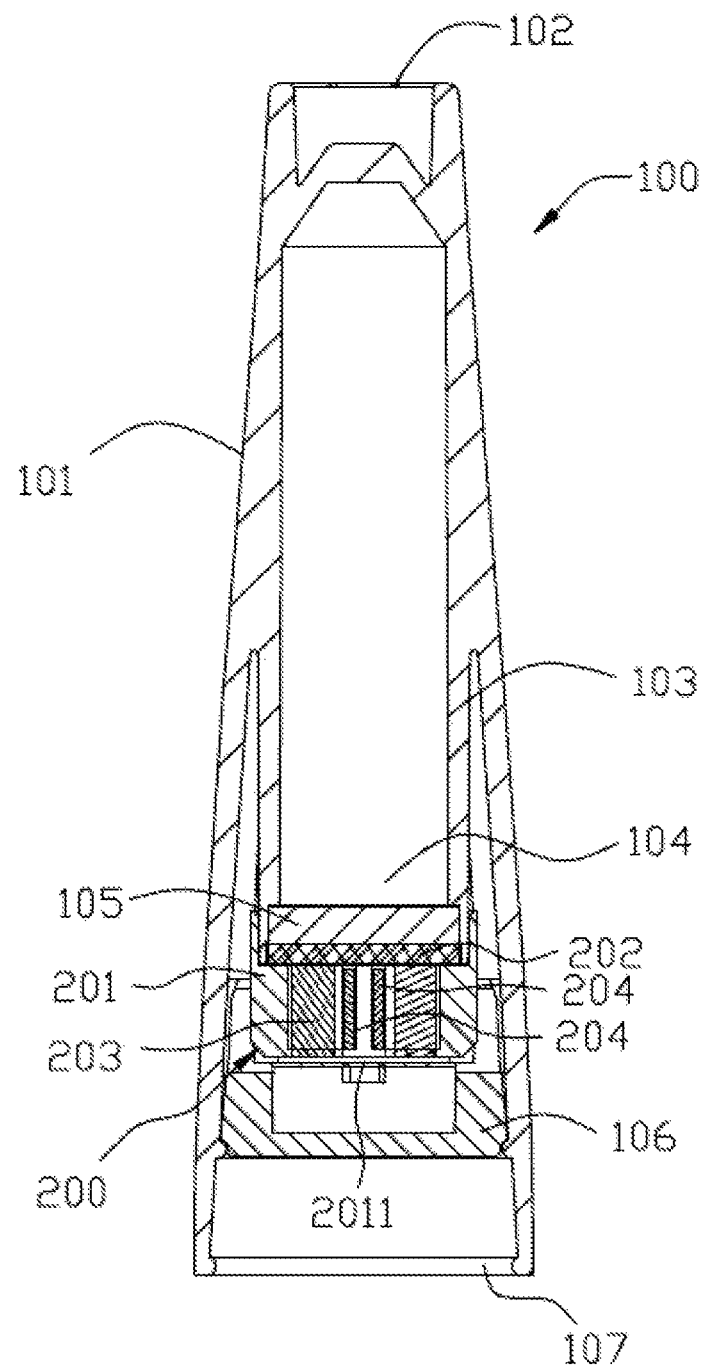
FIG. 1 is an axial cross-sectional view of an atomizer provided in an embodiment.
Figure 2:
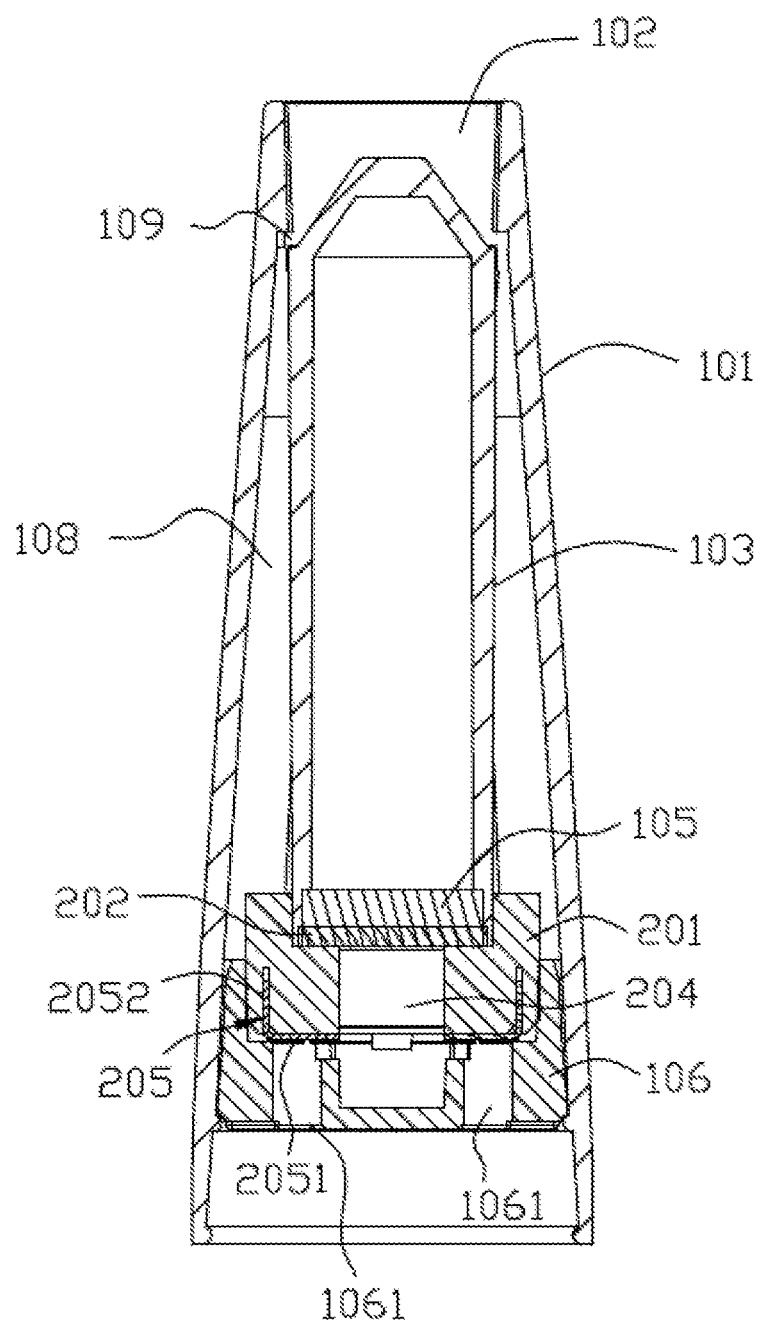
FIG. 2 is an axial sectional view of an atomizer in another cross section in an embodiment.

Referring to FIG. 1 and FIG. 2, the present embodiment provides an atomizer 100 including a housing 101 and a liquid storage cup 103 disposed in the housing 101, an atomizing unit 200, a microporous liquid-conducting body 105, and an air flow channel 108. The housing 101 has a mouthpiece 102 at the top. An air flow channel 108 is provided between the mouthpiece 102 and the atomizing unit 200, and is configured for discharging the aerosol generated in the atomizing unit 200 to the outside of the mouthpiece 102.

The liquid storage cup 103 is configured for storing the tobacco liquid, which may be disposable or reusable. In the present embodiment, the liquid storage cup 103 and the housing 101 are integrally formed. It is to be understood that the liquid storage cup 103 may also be detachably mounted inside the housing 101. An opening 104 is provided at one end of the liquid storage cup 103. The microporous liquid conducting body 105 is plugged inside the opening 104 and is configured for conveying the tobacco liquid in the liquid storage cup 103 to the atomizing unit 200. The atomizing unit 200 is connected to the opening 104 and is located below the microporous liquid conducting body 105.

The above atomizing unit 200 includes a support 201, a liquid guiding component located in the support 201, and at least one vertically arranged heating sheet 204. The heating sheet 204 includes a side surface in contact with the liquid guiding component. The liquid guiding component is configured to be in contact with the microporous liquid conducting body 105 to guide the tobacco liquid to the heating sheet 204. The support 201 further defines an aerosol outlet 2011 configured for discharging the aerosol into the air flow channel 108. Quite usefully, in the present embodiment, the heating sheet 204 is grid-shaped heating sheet or a mesh-shaped heating sheet. The heating sheet 204 has a side surface in contact with the liquid guiding component as a whole and has a large heating area and a high thermal efficiency. The atomizing unit 200 is assembled in the opening 104 of the liquid storage cup 103 as a whole, and the structure is simple.

Quite usefully, in the present embodiment, the liquid guiding component includes a first liquid guiding piece 202 placed horizontally and a second liquid guiding piece 203 placed vertically, the second liquid guiding piece 203 includes a side surface attached to the heating sheet 204, and the first liquid guiding piece 202 is located between the second liquid guiding piece 203 and the microporous liquid conducting body 105 and is horizontally attached to a bottom surface of the microporous liquid conducting body 105. The microporous liquid conducting body 105, the first liquid guiding piece 202 and the second liquid guiding piece 203 form a three-level liquid guiding structure. The tobacco liquid in the liquid storage cup 103 passes through the microporous liquid conducting body 105, the first liquid guiding piece 202 and the second liquid guiding piece 203, and finally reaches the heating sheet 204, which may prevent the tobacco liquid from being conveyed too fast so as to cause leakage.

The conducting speed of the microporous liquid conducting body 105 is faster, but the capability of high temperature resistance is poorer. The first liquid guiding piece 202 and the second liquid guiding piece 203 (that is, the liquid guiding component) may resist a high temperature, may be in direct contact with the heating sheet 204, and also may save a certain amount of tobacco liquid to be gradually supplied to the heating element 204, so that the amount of aerosol generated by heating is constantly uniform.

As a preferred mode, the microporous liquid conducting body is made of PE foam material and/or PET fiber (polyester fiber), and in the present embodiment, it is made of synthetic porous material using PE foam material and PET fiber. Both the first liquid guiding piece and the second liquid guiding piece are made of non-woven fabrics material, and are in particular formed by laminating a plurality of non-woven fabrics. The non-woven fabrics may resist a high temperature and is suitable for direct contact with the heating element 104.

Figure 3:
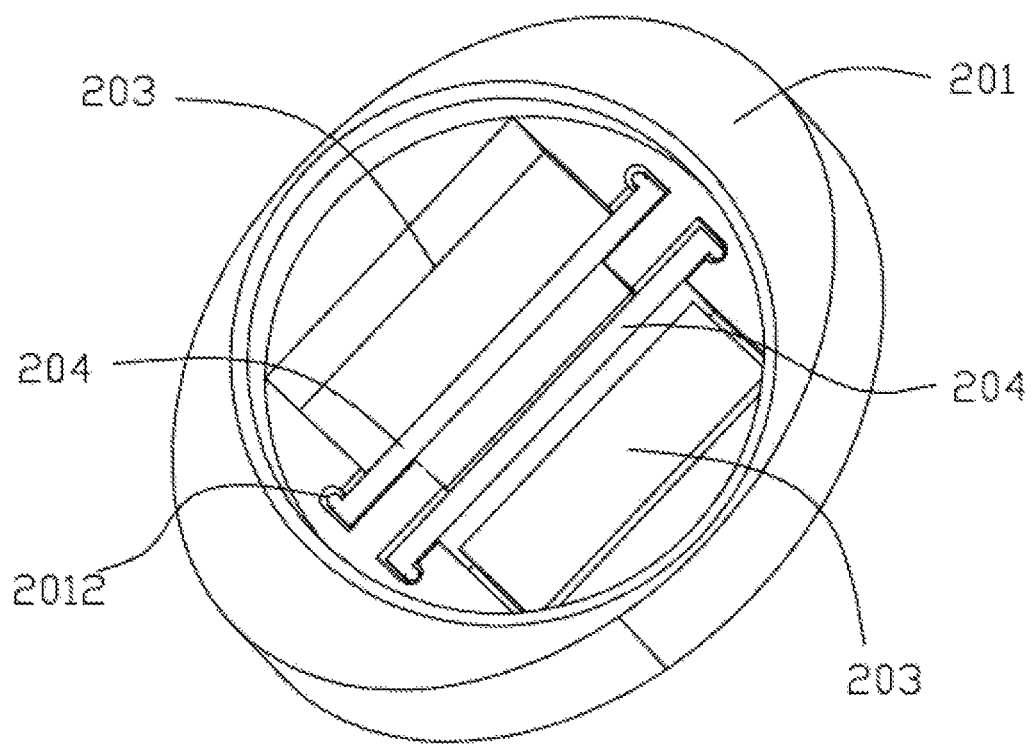
FIG. 3 is a schematic structural view of an atomizing unit involved in an embodiment.
Figure 4:
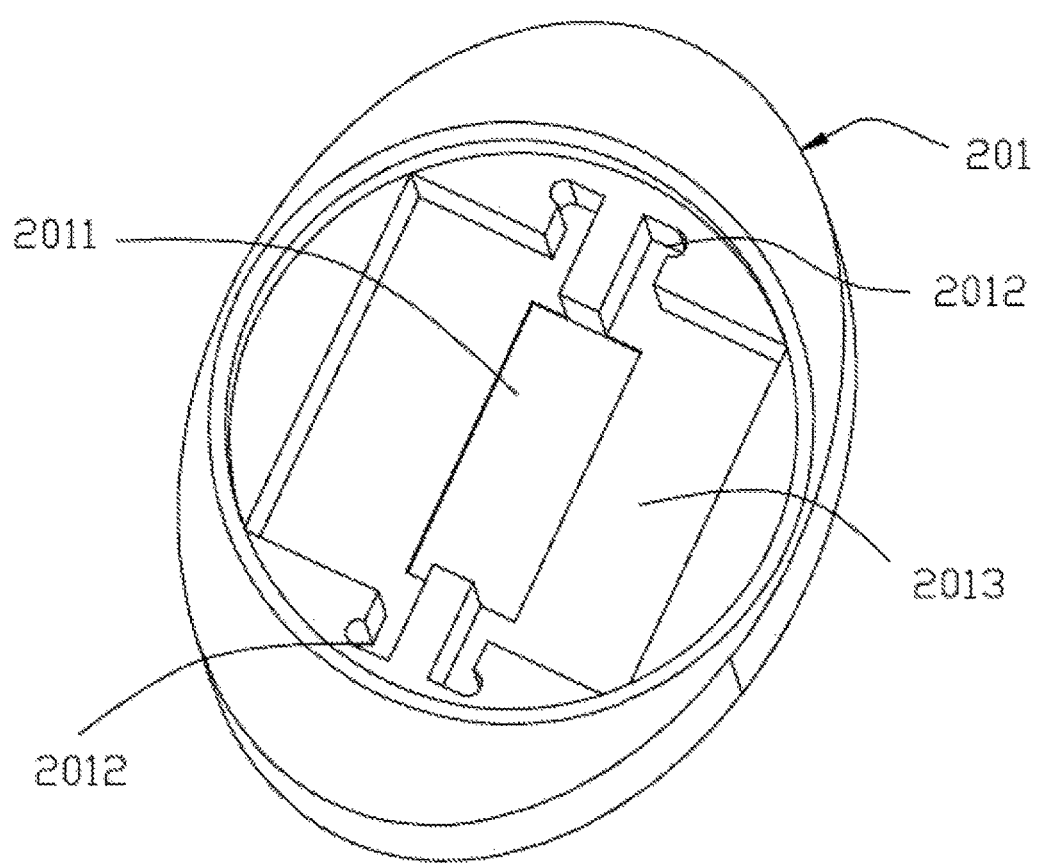
FIG. 4 is a schematic structural view of a support in an embodiment.

As shown in combination with FIG. 1, FIG. 3, and FIG. 4, two heating sheets 204 are vertically arranged inside the support 201, the two heating sheets are spaced apart from each other, and each of the heating sheets 204 matches with a correspondent one of the second liquid guiding pieces 203. The aerosol outlet 2011 is defined at a bottom of the support 201, and the aerosol outlet 2011 is aligned with the two heating sheets 204. Because there is a gap between the two heating elements 204 and the gap is in direct alignment and communication with the lower aerosol outlet 2011, two of the second liquid guiding pieces 203 are respectively distributed on two sides so as to facilitate the aerosol to be promptly discharged into the air flow channel 108. It is to be understood that, in order to increase the amount of aerosol in the atomizing unit 200, more heating sheets may be disposed in the support 201.

As shown in FIG. 4, a heating chamber 2013 is provided in the support 201, and two card slots 2012 are formed on the inner wall of the heating chamber 2013 into which the heating sheets 204 are inserted. Two of the second liquid guiding pieces 203 are provided in the heating chamber 2013, respectively, and are in contact with the corresponding heating sheets 204. In this way, the installation of the atomizing unit 200 is simplified. After the second liquid guiding piece 203 and the heating element 204 are mounted in the heating chamber 2013, the first liquid guiding piece 202 is placed on the upper part of the heating chamber 2013. Finally, the support 201 is assembled at the opening end of the liquid storage cup 103.

Referring to FIG. 2 again, the support 201 is further provided with two electrode sheets 205, respectively, which are in contact with the pins of the heating sheets 204, and the electrode sheets include a contact part 2051 configured to be in contact with an electrode terminal of the power supply and a bending part 2052 configured for inserting into the support 201 to fix the electrode sheets 205. During assembly, the pin of the heating sheet 204 passes through the bottom of the support 201, and then the electrode sheet 205 is mounted on the support 201 and the pin of the heating sheet 204 is compressed. One end of the two electrode sheets 205 is connected to one electrode sheet 205 at the same time, and the other end of the two electrode sheets 205 is connected to another electrode sheet 205.

Quite usefully, a base 106 is further mounted in the housing 101, the base is configured for fixing the atomizing device 200, the base 106 defines two jacks 1061 aligned with the electrode sheets, and the jacks 1061 are adapted to be inserted by electrode terminals of a power supply to come into contact with the electrode sheets 205 to provide power to the heating element 204.

As a preferred solution of the present embodiment, the air flow channel 108 has a size which gradually decreases from downstream to upstream, and has an air flow outlet 109 defined between the housing 101 and the liquid storage cup 103 at an upstream position thereof, and the air flow outlet 109 is communicated with the air flow channel 108 and the mouthpiece 102. The aperture of the air flow outlet 109 is generally smaller. The design that the air flow channel is gradually smaller may allow the air flow to be buffered, and may be conducive for larger droplets in the aerosol to be condensed and flow back to the atomizing unit 200 underneath.

Figure 5:
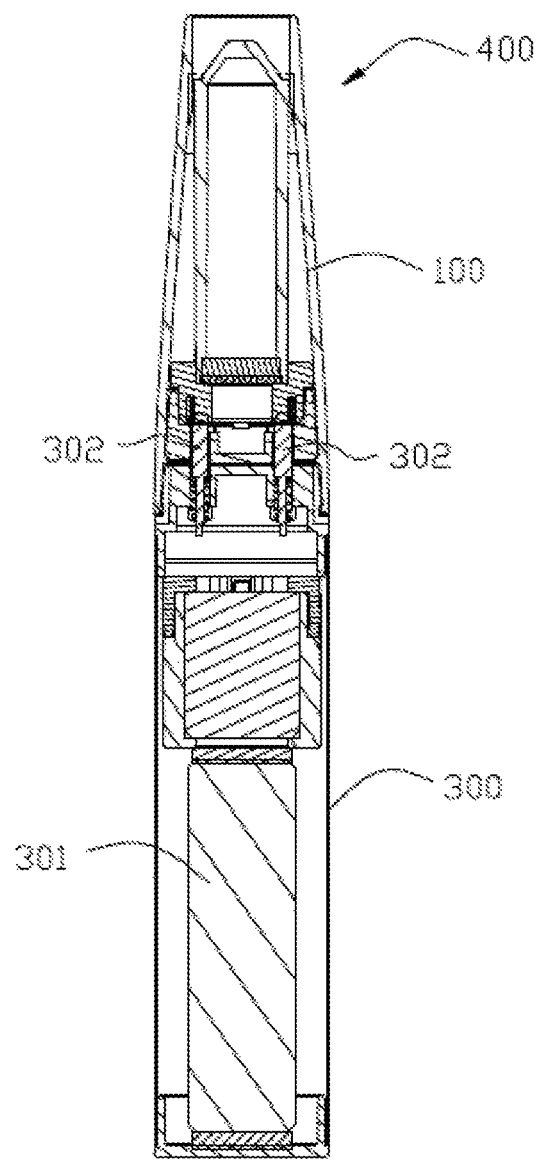
FIG. 5 is a schematic structural view of an electronic cigarette provided in an embodiment.

Referring to FIG. 5, the present embodiment further provides a split-type electronic cigarette 400, including the atomizer 100 described above and a power supply assembly 300 detachably connected to the atomizer 100. The power supply assembly 300 includes an internal battery 301 and a pair of electrode terminals 302, and the two electrode terminals 302 pass through the jacks 1061 described above and are electrically connected to the heating sheet 204 when the power supply assembly 300 is connected to the atomizer 100.

As a preferred solution in the present embodiment, the atomizer 100 and the power supply assembly 300 are connected in a snap fit manner, and an annular rib 107 is provided in an inner edge of a lower end of the housing 101 of the atomizer 100. Of course, It is to be understood that the atomizer 100 and the power supply assembly 300 may be connected in a manner of a common thread, a rotary buckle, a magnetic attraction, and the like.

The above embodiments are only some embodiments of the utility model listed for the sake of easy understanding of the summary of the utility model, and are not intended to limit the technical solutions of the utility model, and not intended to be exhaustive of any possible implementation. Therefore, any minor improvements or equivalent substitutions made to the structures, the flows, or the steps of the utility model should be included in its scope of protection.

What is claimed is:

1. An atomizer, comprising:
   a housing having a mouthpiece thereon;
   a liquid storage cup provided in the housing and configured for storing tobacco liquid, the liquid storage cup having an opening at one end thereof;
   a microporous liquid conducting body plugged inside the opening;
   an atomizing unit connected to the opening and configured for heating the tobacco liquid to generate aerosol, the microporous liquid conducting body being configured for conveying the tobacco liquid in the liquid storage cup to the atomizing unit; and
   an air flow channel provided between the mouthpiece and the atomizing unit;
   wherein the atomizing unit comprises a support, a liquid guiding component located in the support, and at least one vertically arranged heating sheet; the heating sheet comprises a side surface in contact with the liquid guiding component, the liquid guiding component is configured to be in contact with the microporous liquid conducting body to guide the tobacco liquid to the heating sheet, and the support further defines an aerosol outlet configured for discharging the aerosol into the air flow channel.

2. The atomizer according to claim 1, wherein the liquid guiding component comprises a first liquid guiding piece placed horizontally and a second liquid guiding piece placed vertically, the second liquid guiding piece comprises a side surface attached to the heating sheet, and the first liquid guiding piece is located between the second liquid guiding piece and the microporous liquid conducting body and is horizontally attached to a bottom surface of the microporous liquid conducting body.

3. The atomizer according to claim 2, wherein the microporous liquid conducting body is made of PE foam material and/or PET fiber, and both the first liquid guiding piece and the second liquid guiding piece are made of non-woven fabrics material.

4. The atomizer according to claim 2, wherein the atomizer comprises two heating sheets vertically arranged inside the support, the two heating sheets are spaced apart from each other, and each of the heating sheets matches with a correspondent one of the second liquid guiding pieces.

5. The atomizer according to claim 4, wherein the aerosol outlet is defined at a bottom of the support, and the aerosol outlet is aligned with the two heating sheets.

6. The atomizer according to claim 5, wherein a heating chamber is provided in the support, two card slots are formed on the inner wall of the heating chamber into which the heating sheets are inserted, and two of the second liquid guiding pieces are provided in the heating chamber, respectively, and are in contact with the corresponding heating sheets.

7. The atomizer according to claim 1, wherein the support is further provided with two electrode sheets, respectively, which are in contact with the pins of the heating sheets, and the electrode sheets comprise a contact part configured to be in contact with an electrode terminal of the power supply and a bending part configured for inserting into the support to fix the electrode sheets.

8. The atomizer according to claim 7, further comprising a base mounted in the housing, wherein the base is configured for fixing the atomizing device, the base defines two jacks aligned with the electrode sheets, and the jacks are adapted to be inserted by electrode terminals of a power supply to come into contact with the electrode sheets.

9. The atomizer according to claim 1, wherein the air flow channel has a size which gradually decreases from downstream to upstream, and has an air flow outlet defined between the housing and the liquid storage cup at an upstream position thereof, and the air flow outlet is communicated with the air flow channel and the mouthpiece.

10. The atomizer according to claim 1, wherein the heating sheet is a grid-shaped heating sheet or a mesh-shaped heating sheet.

11. An electronic cigarette comprising:
    an atomizer; and
    a power supply assembly detachably connected with the atomizer,
    wherein the atomizer is the atomizer according to claim 1, the power supply assembly comprises a pair of electrode terminals, and the two electrode terminals are configured for electrically connecting to the heating sheet when the power supply assembly is connected to the atomizer.

12. The electronic cigarette according to claim 11, wherein the atomizer and the power supply assembly are connected in a snap fit manner, the housing comprises an annular rib in an inner edge of a lower end of the housing of the atomizer, and the annular rib is configured for forming a snap fit connection.

* * * * *